United States Patent
Duan et al.

(10) Patent No.: US 11,787,826 B2
(45) Date of Patent: Oct. 17, 2023

(54) HYDROCARBYL TIN COMPLEX OF ALKYNYL PHOSPHONIC ACID WITH ANTITUMOR ACTIVITY AND APPLICATION THEREOF

(71) Applicant: Zhejiang Hongsheng Intellectual Property Operation Co., Ltd., Hangzhou (CN)

(72) Inventors: Zhongda Duan, Hangzhou (CN); Jiande Jin, Hangzhou (CN)

(73) Assignee: Zhejiang Hongsheng Intellectual Property Operation Co., Ltd., Hangzhou (CN)

( * ) Notice: Subject to any disclaimer, the term of this patent is extended or adjusted under 35 U.S.C. 154(b) by 82 days.

(21) Appl. No.: 17/061,211

(22) Filed: Oct. 1, 2020

(65) Prior Publication Data
US 2021/0017203 A1    Jan. 21, 2021

(30) Foreign Application Priority Data
Apr. 18, 2020 (CN) .......................... 202010308168.4

(51) Int. Cl.
*C07F 9/38*     (2006.01)
*A61P 35/00*    (2006.01)

(52) U.S. Cl.
CPC ............ *C07F 9/3826* (2013.01); *A61P 35/00* (2018.01)

(58) Field of Classification Search
CPC .................................................... C07F 7/2224
See application file for complete search history.

(56) References Cited

PUBLICATIONS

Yin, Handong, et al. Huaxua Shijii (2000), 22(6), 333-334, 353.*
English translation of Tin, Handong et al. Huaxua Shijii (2000), 22(6), 333-334,353, translation from 2022.*
IUPAC Compendium of Chemical Terminology, Gold Book, Version 2.3.2, pp. 334, 374, 1474 (2012) (Year: 2012).*
F. Ribot et al., 20 Organometallics, 2593-2603 (2001) (Year: 2001).*
R. Shankar et al., 53 Inorganic Chemistry, 6195-6203 (2014) (Year: 2014).*
C. Diop et al., 25 Main Group Metal Chemistry, 683-689 (2002) (Year: 2002).*

* cited by examiner

*Primary Examiner* — Alexander R Pagano

(57) ABSTRACT

Hydrocarbyl tin complexes of alkynyl phosphonic acid with antitumor activity and their application are provided. Tests are conducted to evaluate activity, showing that the provided complexs have much stronger activity than cisplatin. The provided hydrocarbyl tin complexes can be potential candidate as a clinical antitumor drug.

7 Claims, No Drawings

HYDROCARBYL TIN COMPLEX OF ALKYNYL PHOSPHONIC ACID WITH ANTITUMOR ACTIVITY AND APPLICATION THEREOF

CROSS REFERENCE TO RELATED APPLICATION

The application claims the priority of the Chinese patent application filed on Apr. 18, 2020, with the application number of 202010308168.4 and the invention title of "HYDROCARBYL TIN COMPLEX OF ALKYNYL PHOSPHONIC ACID WITH ANTITUMOR ACTIVITY AND APPLICATION THEREOF", the entire contents of which are incorporated herein by reference.

TECHNICAL FIELD

The present invention relates to a hydrocarbyl tin complex of alkynyl phosphonic acid with antitumor activity, and belongs to the field of pharmaceutical chemistry.

BACKGROUND TECHNOLOGY

The phosphonic (phosphoric) acid derivatives of hydrocarbyl tin have attracted great attention due to their strong insecticidal, bactericidal, herbicidal and other biological activities. There are some literatures about the study of hydrocarbyl tin complex of alkynyl phosphonic acid, but most of them focus on the synthesis and structure research stage, yet there are few researches on its pharmacological activities. Furthermore, most of them are intended for their bactericidal and acaricidal activities, yet few researches are conducted to find out their antitumor activities.

SUMMARY OF THE INVENTION

The present invention provides a hydrocarbyl tin complex of alkynyl phosphonic acid with antitumor activity, to explore new antitumor drugs.

On the basis of full investigation of the prior art, the present invention screens out new hydrocarbyl tin complex of alkynyl phosphonic acid with antitumor activity, so as to provide a new candidate for antitumor compound.

In order to achieve the above purpose, the technical solution of the present invention is realized as follows:

A tin complex of alkynyl phosphonic acid with antitumor activity is provided, having the following structure:

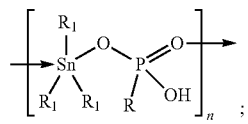

wherein, $R_1$ is selected from n-butyl, t-butyl, phenyl, benzyl, p-chlorobenzyl and dimethylbenzyl;

and $R_2$ is a randomly substituted alkyl, aryl and heteroaryl; n is an integer from 2.

Further, $R_2$ is a randomly substituted C1-C4 alkyl, C6-C10 aryl and C6-C10 heteroaryl.

Further, $R_2$ is a randomly substituted phenyl; and the substituent of $R_2$ is a halogen, such as F, Cl, Br, I; a C1-C8 alkyl, such as methyl, ethyl, propyl, t-butyl; a C1-C8 alkoxy, such as methoxy, ethoxy, propoxy, t-butoxy; nitryl, cyano group, trifluoromethyl; and the number of the substituents is 1, 2, 3, 4, or 5.

The above-mentioned tin complexes of alkynyl phosphonic acid are used for the preparation of antitumor drugs, which are specifically targeted for cervical cancer, breast cancer, lung adenocarcinoma, liver cancer, prostate cancer, colon cancer, etc.

The complexes of the present invention have the following beneficial effects:

In the present invention, the structure of the tin complexes of alkynyl phosphonic acid is modified, and several compounds with antitumor activity are screened out therefrom, which show much stronger activity than cisplatin, especially for human lung cancer, so it is a candidate to be a potential clinical anticancer drug. During the experiment, it is found that the change of the alkyl part ($R_1$) in the hydrocarbyl tin had a greater influence on the biological activity of the complexes, and the n-butyl has the best effect; and the kinds of substituents on the benzene ring also contribute a lot to its biological activity.

DETAILED DESCRIPTION OF THE EMBODIMENTS

In order to make the purpose, technical solution and advantages of the present invention clearer, the representative embodiments of the present invention will be described in detail below, but the present invention is not limited thereto.

The present invention provides a hydrocarbyl tin complex of alkynyl phosphonic acid with antitumor activity, having the following structure:

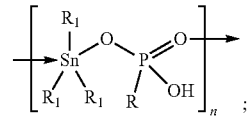

wherein, $R_1$ is selected from n-butyl, t-butyl, phenyl, benzyl, p-chlorobenzyl and dimethylbenzyl;

and $R_2$ is a randomly substituted alkyl, aryl and heteroaryl; n is an integer from 2.

In some embodiments, $R_1$ can be n-butyl, t-butyl, phenyl, benzyl; $R_2$ can be a randomly substituted alkyl, aryl and heteroaryl. $R_2$ can be randomly substituted by 1 to 5 substituents selected from the group consisting of halogen, $C_1$-$C_8$ alkyl, $C_1$-$C_8$ alkoxy, nitryl, cyano group, and trifluoromethyl. More specifically, $R_2$ can be randomly substituted by 1 to 5 substituents selected from the group consisting of halogen, such as F, Cl, Br, I; a $C_1$-$C_8$ alkyl, such as methyl, ethyl, propyl, t-butyl; a $C_1$-$C_8$ alkoxy, such as methoxy, ethoxy, propoxy, t-butoxy, nitryl, cyano group, trifluoromethyl.

In other embodiments, $R_1$ can be n-butyl, benzyl; $R_2$ can be a randomly substituted alkyl, aryl and heteroaryl. $R_2$ can be randomly substituted by 1 to 5 substituents selected from the group consisting of halogen, C1-C8 alkyl, C1-C8 alkoxy, nitryl, cyano group, and trifluoromethyl. Among them, halogen can be F, Cl, Br, I; $C_1$-$C_8$ alkyl can be methyl, ethyl, propyl, t-butyl, $C_1$-$C_8$ alkoxy can be methoxy, ethoxy, propoxy, t-butoxy.

In other embodiments, $R_2$ can be C1-C4 alkyl, C6-C10 aryl and C6-C10 heteroaryl randomly substituted by 1 to 5 substituents selected from methyl, ethyl, propyl, tert-butyl, methoxy, ethoxy, propoxy, tert-butylene, nitryl, cyano group, trifluoromethyl.

More preferably, $R_2$ is a phenyl randomly substituted by 1 to 5 substituents selected from methyl, methoxy, nitryl, cyano group, trifluoromethyl.

More preferably, $R_2$ is a phenyl randomly substituted by 1 to 5 substituents selected from methyl and trifluoromethyl.

In other embodiments, $R_1$ can be n-butyl, t-butyl, phenyl, benzyl; $R_2$ can be C1-C4 alkyl, C6-C10 aryl and C6-C10 heteroaryl randomly substituted by 1 to 5 substituents selected from methyl, methoxy, nitryl, cyano group, trifluoromethyl.

In other embodiments, $R_1$ can be n-butyl, benzyl; $R_2$ can be phenyl randomly substituted by 1 to 5 substituents selected from methyl and trifluoromethyl.

Embodiment 1: The Synthesis of Tri-n-butyltin (IV) (3,5-dimethylphenyl) Acetylenyl Phosphonic Acid Derivatives

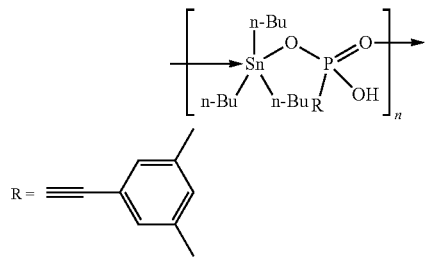

The structural formula of the product is shown as above:
In a 100 ml round-bottom flask, 3 mmol of tri-n-butyl tin chloride and 20 ml of anhydrous methanol were added. The tri-n-butyl tin chloride was completely dissolved with stirring. After that, 3.2 mmol of (3,5-dimethylphenyl) ethynylphosphate monosodium was added. Reaction of the mixture in the flask was held for 5 hours under reflux with stirring, then cooled and the filtrate of the reaction solution was concentrated under reduced pressure. An appropriate amount of petroleum ether was added into the concentrated filtrate. After filtering, vacuum concentration was performed to obtain the product, wherein the yield is 85%.

Element Analysis Data: Anal. Calcd. For $C_{22}H_{37}O_3PSn$ (%): C 53.02, H 7.58, Sn 23.95; Found (%): C 52.98, H 7.41, Sn 23.69. Nuclear Magnetic Resonance Spectroscopy Data ($^1$H NMR/δ): 0.79-0.83(15H), 1.24-2.03(18H), 7.21-7.89 (3H).

Embodiment 2

According to the method used in embodiment 1, tri-n-butyltin (IV) (3-Trifluoromethyl Phenyl) acetylenyl phosphonic acid derivatives are prepared with phenylacetylenyl phosphate monosodium as raw material.

Embodiment 3: Antitumor Activity Test of the Compounds

The compound produced in embodiment 1 is named as "Compound 1", and the compound produced in embodiment 2 is named as "Compound 2".

MCF-7, HT-29, A549 and HepG2 cells are got from American Tissue Culture Collection, which are cultured with the culture medium containing 10% bovine fetal serum in a $CO_2$-containing incubator at 37° C. MTT method is used to detect cell proliferation and growth inhibition. The number of experimental cells is adjusted to obtain the absorbance at 570 nm. 6 concentrations are set for the compound test solution (0.1 nmol/L~10 μmol/L). The cells are treated for 72 hours. At least 3 parallel experiments and 3 repeated experiments are conducted for each concentration. The $IC_{50}$ value is determined by statistical analysis.

The inventors of this application make appropriate structural improvement and screening from existing hydrocarbyl tin complex of alkynyl phosphonic acid on the basis of existing literature, so as to explore new antitumor drugs. According to the preliminary biological activity test, it shows that this kind of hydrocarbyl tin complex of alkynyl phosphonic acid do possess antitumor activity. Among them, several specially-structured complexes especially show excellent activity.

Taking cisplatin as the contrast, the in vitro growth inhibitory activity of Compound 1 and Compound 2 on tumor cells are tested, including MCF7 (human breast cancer cells), HT-29 (human colon cancer cells), A549 (human lung cancer cells) and HepG2 (liver cancer cells). The results are shown in the table below. It is found that the compounds show stronger antitumor activity than cisplatin, especially for the inhibition of A549, and can be used as candidate anticancer compounds.

TABLE 1

| Compound | IC$_{50}$ Value (μmol/L) | | | |
| --- | --- | --- | --- | --- |
| | MCF7 | HT-29 | A549 | HepG2 |
| 1 | 0.194 | 0.635 | 0.033 | 0.211 |
| 2 | 1.732 | 0.962 | 0.274 | 0.872 |
| Cisplatin | 43 | 35 | 1.3 | 17 |

We claim:
1. A hydrocarbyl tin complex of alkynyl phosphonic acid with antitumor activity, characterized by having the following structure:

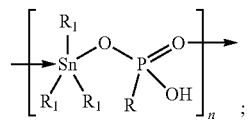

wherein, R1 is selected from the group consisting of n-butyl, t-butyl, phenyl, benzyl, p-chlorobenzyl and dimethylbenzyl;

and R2 is a randomly substituted alkyl, aryl and heteroaryl wherein the alkyl, aryl or heteroaryl is substituted with 1 to 5 substituents selected from the group consisting of nitryl, cyano group, and trifluoromethyl, n is an integer from 2.

2. The hydrocarbyl tin complex of alkynyl phosphonic acid according to claim 1, wherein, R2 is a randomly substituted C1-C4 alkyl, C6-C10 aryl and C6-C10 heteroaryl.

3. The hydrocarbyl tin complex of alkynyl phosphonic acid according to claim 1, wherein, R2 is a randomly substituted phenyl.

4. The hydrocarbyl tin complex of alkynyl phosphonic acid according to claim 1, wherein,
R2 is randomly substituted by 1 to 5 trifluromethyl groups.

5. The hydrocarbyl tin complex of alkynyl phosphonic acid according to claim 3, wherein, R2 is randomly substituted by 1 to 5 trifluoromethyl groups.

6. The hydrocarbyl tin complex of alkynyl phosphonic acid according to claim 1, wherein, R1 is selected from n-butyl and benzyl.

7. The hydrocarbyl tin complex of alkynyl phosphonic acid according to claim 3, wherein, R1 is selected from n-butyl and benzyl.

\* \* \* \* \*